United States Patent [19]

Wolff

[11] Patent Number: 4,703,184
[45] Date of Patent: Oct. 27, 1987

[54] SKIN TANNING APPARATUS

[76] Inventor: Friedrich Wolff, Störklingasse 38, CH-4125 Riehen/Basel, Switzerland

[21] Appl. No.: 844,009

[22] Filed: Mar. 25, 1986

[51] Int. Cl.⁴ ............................................. A61N 5/06
[52] U.S. Cl. .............................. 250/504 R; 250/494.1; 250/492.1; 128/396; 128/373
[58] Field of Search ............. 250/504 R, 494.1, 493.1, 250/492.1; 313/112; 128/396, 395, 373, 372

[56] References Cited

U.S. PATENT DOCUMENTS

| | | | |
|---|---|---|---|
| 4,095,113 | 6/1978 | Wolff | 250/494 |
| 4,106,083 | 8/1978 | Wolff | 362/217 |
| 4,177,384 | 12/1979 | Wolff | 250/494 |
| 4,194,125 | 3/1980 | Wolff | 250/504 |
| 4,196,354 | 4/1980 | Wolff | 250/494 |
| 4,287,554 | 9/1981 | Wolff | 362/218 |
| 4,309,616 | 1/1982 | Wolff | 250/494 |
| 4,316,094 | 2/1982 | Wolff | 250/504 R |
| 4,349,765 | 9/1982 | Brändli | 313/112 |
| 4,623,796 | 11/1986 | Kratz | 250/504 R |

FOREIGN PATENT DOCUMENTS 2743079 4/1979 Fed. Rep. of Germany .
2831013 1/1980 Fed. Rep. of Germany .
8406682.2 10/1984 Fed. Rep. of Germany .

Primary Examiner—Craig E. Church
Assistant Examiner—Jack I. Berman
Attorney, Agent, or Firm—Peter K. Kontler

[57] ABSTRACT

Full-sized skin tanning apparatus has a row of twelve parallel long tubular radiation emitting lamps and five shorter lamps which alternate with the four centrally located longer lamps and emit radiation in the region of the head of an adult person who is tanning her or his skin. The lamps emit ultraviolet radiation primarily or exclusively in the UVA range and emit no radiation in the UVC range. The shorter lamps cooperate with the adjacent portions of the longer lamps to tan the skin on the face more intensively than the skin on other parts of the body which is tanned by the longer lamps.

18 Claims, 5 Drawing Figures

SKIN TANNING APPARATUS

CROSS-REFERENCE TO RELATED CASES

Sunlamps which can be used in the apparatus of the present invention are disclosed in commonly owned copending patent applications Ser. Nos. 752,251 (filed July 3, 1985) and 770,723 (filed Aug. 29, 1985).

Attention is invited to commonly owned U.S. Pat. Nos. 4,095,113, 4,106,083, 4,177,384, 4,194,125, 4,196,354, 4,287,554, 4,309,616 and 4,316,094.

BACKGROUND OF THE INVENTION

The invention relates to improvements in apparatus for exposing the skin of a patient or a healthy person to radiation. More particularly, the invention relates to improvements in apparatus which emit ultraviolet radiation for purely medical, purely cosmetic or cosmetic and medical purposes.

It is known to provide a skin tanning or psoriasis-treating apparatus with a set of elongated tubular lamps which are installed parallel to each other on a suitable support to emit ultraviolet radiation, primarily or exclusively in the UVA range, within an area large enough to accommodate the entire body of a male adult. The neighboring lamps are separated from each other by relatively narrow elongated gaps of uniform width to thus ensure that the skin of the user is exposed to highly uniform radiation. The emission spectrum of the lamps covers the UVA range and, if necessary, a small percentage of the UVB range but such lamps emit no radiation at all in the UVC range. Reference may be had to numerous United States and foreign patents of the applicant.

It is also known to equip such apparatus with means for intensifying, or increasing the amounts of, radiation which is to reach the skin on the head (particularly on the face) of a patient or a healthy person who desires to acquire a quick tan without risking a sunburn or other unpleasant consequences of exposure to ultraviolet radiation. The reason for the provision of radiation intensifying means is that the skin on the faces of many persons is less sensitive to radiation than the skin on the torso and on the extremities. Therefore, such persons can expose their faces to ultraviolet radiation in quantities considerably exceeding those which can safely reach the skin on other parts of the body.

It is further known to provide a selected portion of a skin tanning apparatus with a high-pressure burner which emits radiation in the UVA range at an intensity greatly exceeding that of radiation which is emitted by standard tubular lamps. The burner is installed between two groups of longer lamps and in line with a group of shorter lamps. The length of the longer lamps is 176 cm and the length of the shorter lamps is in the range of 150 cm. A drawback of such apparatus is that the intensity of radiation issuing from the shorter lamps is much less pronounced than the intensity of radiation which issues from the longer lamps. This applies even if the energy input per unit length of a longer and a shorter lamp is the same. The result is that the tanning effect of the apparatus is not uniform, i.e., the skin on the face is exposed to maximum amounts of radiation and the remaining skin is subjected to radiation of greater intensity (long lamps) as well as to radiation of lesser intensity (shorter lamps). Another drawback of the just described apparatus is that the burner requires a certain amount of time before it begins to emit radiation at a maximum rate as well as a certain amount of time prior to terminating the emission of radiation upon disconnection from the energy source. Still further, the life span of the burner is only about half the useful life of the lamps, and the burner generates substantial amounts of heat so that the apparatus must be equipped with additional heat filtering means.

As a rule, a full-sized apparatus has an effective width of 60–70 cm and employs between 10 and 12 radiation-emitting tubular lamps each having a length of 176 cm. Each lamp has a diameter of 38 mm and the width of the gaps between neighboring lamps is between 20 and 25 mm. Such apparatus cannot emit additional radiation for more intensive tanning of the skin on the face of a person.

Certain apparatus for emission of visible light employ so-called miniature lamps each of which is U-shaped, i.e., it has two parallel elongated legs and an arcuate web connecting one end of one leg with one end of the other leg. The other ends of the legs constitute or carry terminals which are insertable into suitable socket means for connection with an energy source.

The prior art which was cited in the corresponding German patent application includes German Utility Model No. 84 06 682 and published German patent applications Nos. 27 43 079 and 28 31 013. The Utility Model discloses an apparatus with a UVA high-pressure burner. The application No. 27 43 079 discloses an apparatus wherein the lamps are staggered with reference to each other. The application No. 28 31 013 discloses an apparatus wherein the reflectors have slots for the flow of hot air from the lamps to one or more fans.

OBJECTS AND SUMMARY OF THE INVENTION

An object of the invention is to provide an apparatus for tanning and/or for medical treatment of the skin with novel and improved means for ensuring the exposure of the face of the user to more intensive ultraviolet radiation, primarily or exclusively in the UVA range.

Another object of the invention is to provide an apparatus which need not employ a high-pressure burner.

A further object of the invention is to provide the apparatus with a novel array of elongated tubular lamps and with novel and improved means for reflecting radiation which issues from such lamps.

An additional object of the invention is to provide an apparatus which can subject the skin on the face of the user to highly uniform radiation in the selected range of the ultraviolet spectrum.

Still another object of the invention is to provide the apparatus with novel and improved means for preventing radiation which issues from one or more groups of radiation sources from interfering or from pronouncedly interfering with radiation which issues from the remaining source or sources of radiation.

An additional object of the invention is to provide a relatively simple and inexpensive apparatus which can be rapidly converted from operation with uniform radiation to operation with more intensive radiation upon the skin on the face of the user or vice versa.

The invention resides in the provision of an apparatus for transmitting radiation to the entire body of an adult, i.e., in the provision of an apparatus which can irradiate an average adult (and hence also a shorter person) from the top of the head to toes. The apparatus comprises a support (e.g., a lounge chair-like floor- or ground-supported part or an elongated roof-like device which can be mounted at a level above the place occupied by a prone male or female adult or a shorter person who is to be exposed to ultraviolet radiation for the purpose of tanning and/or healing her or his skin. The apparatus further comprises a set of spaced-apart parallel first elongated tubular lamps which are mounted in the support and are designed to emit ultraviolet radiation primarily or exclusively in the UVA range with little or no emission in the UVB range and no emission in the UVC range. The neighboring first lamps define elongated gaps of predetermined width. Still further, the apparatus comprises means for intensifying (and more specifically for adding to) the radiation which reaches the head of the person who is exposed to radiation issuing from the first lamps. Such radiation intensifying or amplifying means comprises a set of second elongated tubular lamps whose emission spectra preferably match or closely approximate the emission spectra of the first lamps. The second lamps are mounted in or on the support and are shorter than the first lamps; they are installed in selected gaps so that radiation which issues therefrom is added to radiation issuing from the adjacent portions of certain first lamps.

The first lamps include first and second outer lamps (e.g., four first and four second outer lamps) and a number (e.g., four) of intermediate lamps between the first and second outer lamps. The length of intermediate lamps preferably matches the length (e.g., 176 cm) of the outer lamps. The second lamps alternate with the intermediate lamps, and each second lamp is adjacent to one end of the neighboring intermediate lamp or lamps. The diameter of each second lamp need not exceed 22 mm (it is preferably in the range of 15 mm), and the length of each second lamp can be between 400 and 500 mm.

Each second lamp can constitute a U-shaped body with two free ends received in sockets of the support. Additional sockets of the support receive the ends of the first lamps. The arrangement is preferably such that the sockets for the free ends of the second lamps form a first row, that the sockets for the first longitudinal ends of the first lamps form a second row and the sockets for the second ends of the first lamps form a third row between the first and second rows.

The total number of first lamps can be between 9 and 13, and the total number of second lamps can be between 3 and 7.

Reflectors can be provided on the support between each second lamp and the neighboring first lamps; each such reflector can have a first surface which reflects radiation issuing from the respective (adjacent) first lamp and a second surface which reflects radiation issuing from the respective (adjacent) second lamp.

Alternatively or in addition, a one-piece reflector can be placed behind the second lamps and the adjacent portions of those first lamps which alternate with the second lamps. The reflector has a radiation-reflecting surface which faces the second lamps and the aforementioned portions of the first lamps, and such reflector can have an elongated ridge behind each second lamp and/or behind the portion of each adjacent first lamp.

Each second lamp preferably emits ultraviolet radiation only (exclusively) in the UVA range. The first and second lamps are, or can be, standard-size lamps. Such lamps are disposed below a light-transmitting support if the radiation is directed upwardly toward the body of the person seeking a tan, and the lamps are disposed below or between two halves of the support if the person seeking a tan assumes a position at a level below the two sets of lamps.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
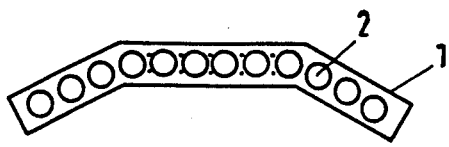
FIG. 1 is a schematic transverse sectional view of a skin tanning apparatus which embodies one form of the invention.
Figure 2:
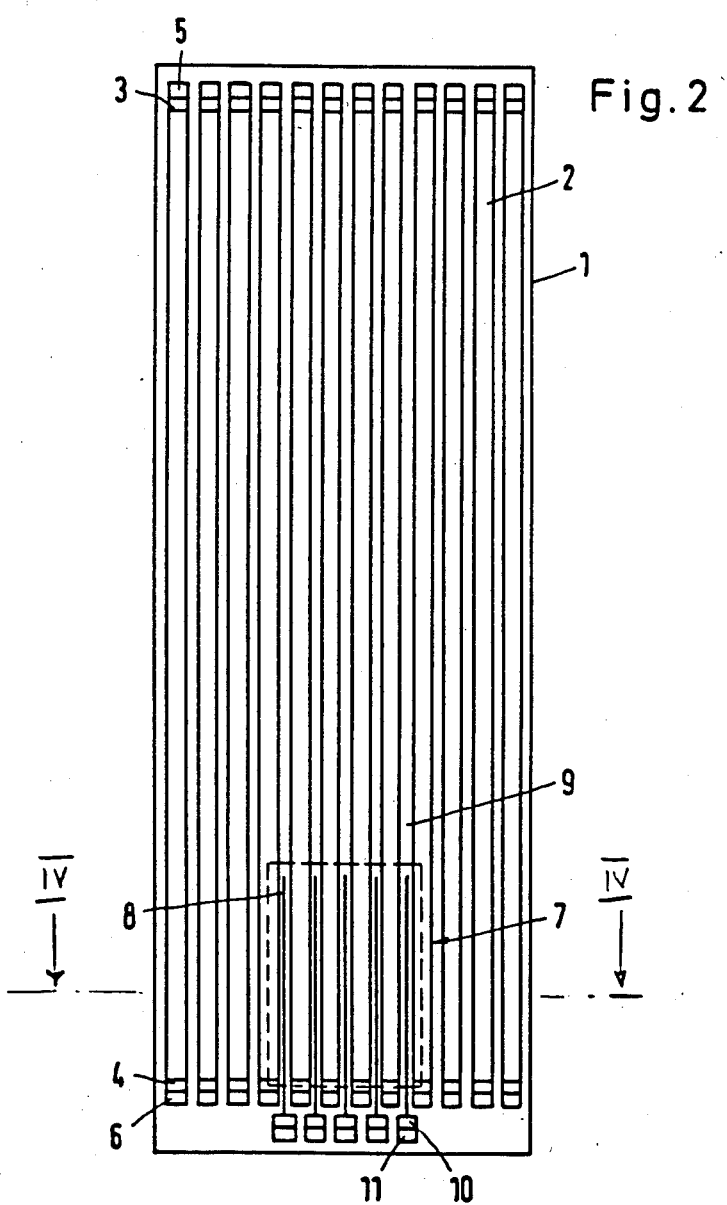
FIG. 2 is a bottom plan view of the apparatus which is shown in FIG. 1.

FIGS. 1 and 2 show an apparatus which is designed to emit radiation toward the entire body of a prone person occupying the space below a set of twelve spaced-apart elongated lamps 2 each having a standard length (176 cm). The end portions 3 and 4 of each lamp are received in sockets 5 and 6 which are provided in a support 1 constituting a suitably configured cover or hood at a level above the set of lamps 2. The person who wishes to tan her or his skin occupies a bed or a lounge chair below the lamps 2. Each lamp 2 has a diameter D of 38 mm and is designed to emit primarily ultraviolet radiation, preferably primarily or exclusively in the UVA range. The arrangement may be such that the lamps 2 emit ultraviolet radiation 99.5 percent of which is in the UVA range and 0.5 percent of which is in the UVB range (i.e., no radiation at all in the UVC range) if the apparatus is designed for skin tanning. If the apparatus is used for medical purposes (particularly for the treatment of psoriasis), the percentage of radiation in the UVC range remains zero and the share of radiation in the UVB range is increased to approximately 2 percent.

Standard lamps of the just outlined character emit radiation quite uniformly over the entire body of a patient or a person seeking a quick tan.

The length of the support 1 equals or approximates 2 m and its width is approximately 0.7 m. The width a of gaps 9 between the lamps 2 is between 20 and 22 mm.

The area 7 within the broken-line rectangle shown in the lower part of FIG. 2 is occupied by the head of the user of the improved apparatus. Thus, if the user faces upwardly, her or his face is exposed to radiation issuing from the respective end portions of the four intermediate lamps 2 and the adjacent innermost right-hand and left-hand outer lamps. There are four left-hand and four right-hand outer lamps.

Figure 3:
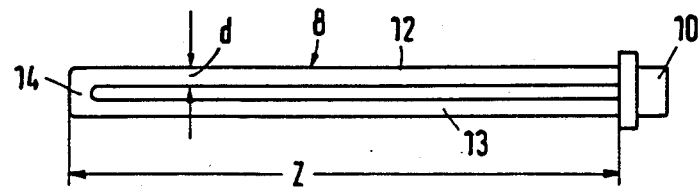
FIG. 3 is an enlarged schamtic side elevational view of a U-shaped second lamp.

The area 7 further accommodates four standard miniature lamps (second lamps) 8 each having a length Z of between 400 and 500 mm, preferably 443 mm, and a diameter d of less than 22 mm, preferably 15 mm. The lamps 8 are mounted on the support 1 in the gaps 9 between the adjoining lamps 2 at the respective end of the support 1. Each lamp 8 is a U-shaped body (see FIG. 3) whose free ends 10 are received in complementary sockets 11 of the support 1. The row of sockets 6 is disposed between the rows of sockets 5 and 11, i.e., the free ends 10 of the lamps 8 extend outwardly of the respective gaps 9 and beyond the adjacent ends 4 of the longer lamps 2. Such placing of the sockets 11 facilitates the insertion and detachment of the free ends 10. Each U-shaped lamp 8 has two parallel elongated sections or legs 12, 13 and an arcuate web 14 which constitutes a connection between the respective ends of the legs 12, 13. The sockets 10 at the other ends of the legs 12, 13 (i.e., at the two free ends of the lamps 8) can be united to form a single socket.

Figure 4:
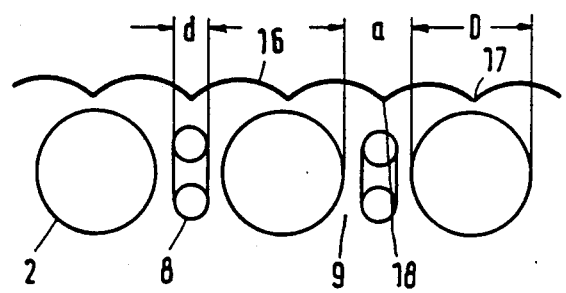
FIG. 4 is an enlarged fragmentary transverse sectional view as seen in the direction of arrows from the line IV—IV of FIG. 2.

The radiation-emitting material of the lamps 8 is preferably identical with the radiation-emitting material of the lamps 2. At any rate, the spectrum which is generated by each of the lamps 8 is or can be similar to or identical with the spectrum which is generated by a lamp 2. As shown in FIG. 4, the lamps 8 are installed in the respective gaps 9 in such a way that the legs 12 are disposed at a level above the legs 13 (or vice versa); this renders it possible to accommodate such lamps in gaps 9 whose width need not exceed 22 mm.

FIG. 4 further shows a reflector 16 whose light-reflecting surface faces toward the lamps 2, 8 and which has an elongated ridge 17 behind each lamp 2 and a similar elongated ridge 18 behind each lamp 8. The reflector 16 is mounted at the underside of the support 1 within the area 7. A simpler reflector (not specifically identified) without the ridges 18 can be provided behind the lamps 2 in the U-shaped area outside of the area 7.

The intensity of radiation to which the face of the user of the improved apparatus is exposed is increased by the amount of radition issuing from the lamps 8 and impinging directly, or being reflected, onto the face.

Figure 5:
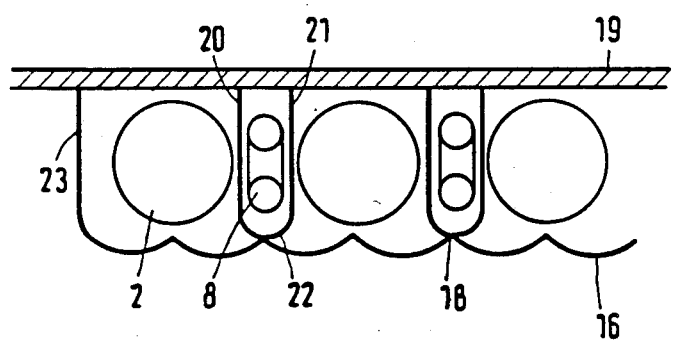
FIG. 5 is a similar fragmentary transverse sectional view of a modified apparatus wherein the lamps are located at a level above the support.

FIG. 5 shows a portion of a modified apparatus with a plate-like support 19 for the body of a person. The support 19 transmits ultraviolet radiation in the UVA range but need not transmit such radiation in the UVC range. The orientation of the lamps 8 with reference to the lamps 2 is or can be the same as described in connection with FIG. 4. The reflector 16 of FIG. 5 is analogous to the reflector of FIG. 4 except that it comprises end portions 23 which are secured to the support 19. The apparatus of FIG. 5 further comprises U-shaped additional reflectors 20, 21 each of which extends between a lamp 8 and the adjacent lamp 2. The reflectors 20 are or can be integral with the adjacent reflectors 21 to form U-shaped bodies having webs 22 which are affixed to or simply rest on the adjacent ridges 18 of the main reflector 16. Each of the reflectors 20, 21 has a first surface which reflects radiation issuing from the adjacent lamp 2 and a second surface serving to reflect radiation which issues from the adjacent lamp 8. The reflectors 16, 20, 21 constitute props and reinforcing or stiffening means for the plate-like support 19.

FIG. 1 shows that the lamps 2 are divided into three groups with each group disposed in a different plane. However, it is also within the purview of the invention to mount all twelve lamps 2 in a common plane. The configuration which is shown in FIG. 1 is preferred at this time because it ensures more uniform tanning of skin on the entire body of the user.

An important advantage of the improved apparatus is that the intensity of radiation which is emitted by the lamps 2 is constant in each part of the irradiated area. Thus, the intensity of radiation in the area 7 can be calculated with a high degree of accuracy. Moreover, the small-diameter lamps 8 can be readily fitted into the gaps 9, and the spectra of the lamps 8 need not deviate from those of the lamps 2. All this contributes to simplicity and lower cost of the apparatus.

The apparatus could employ relatively short lamps 8. However, a length Z in the range of between 400 and 500 mm is preferred at this time because the apparatus can be used with advantage by shorter as well as by taller persons.

The utilization of U-shaped lamps 8 is desirable because this contributes to the intensity of radiation in the area 7. Though the leg 12 interferes with the propagation of radiation from the leg 13 toward the person using the apparatus, a substantial percentage of radiation issuing from the leg 13 is still capable of reaching the body of the user. Moreover, and since the combined length of the legs 12 and 13 is between 800 and 1000 mm, the intensity of radiation per unit length of a lamp 8 is much more pronounced than in the case of a lamp with a single leg having a length of between 400 and 500 mm. As mentioned above, the provision of a common socket 11 for the terminal 10 which is common to the free ends of the legs 12 and 13 contributes to simplicity of the support 1.

The placing of sockets 11 outwardly of the row of sockets 6 exhibits the advantage that the width of each terminal 10 can exceed the width a of a gap 9. Moreover, radiation issuing from the legs 12, 13 in the regions of the respective sockets 11 extends outwardly beyond the row of sockets 6.

The provision of ridges 17, 18 and additional reflectors 20–22 contributes to greater intensity of the radiation.

The utilization of lamps which emit ultraviolet radiation only in the UVA range is desirable in tanning apparatus because this ensures rapid tanning. If a certain amount of radiation in the UVB range is desirable for tanning, such radiation is available in that which issues from the lamps 2 in the area 7.

Without further analysis, the foregoing will so fully reveal the gist of the present invention that others can, by applying current knowledge readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. Apparatus for transmitting radiation to the entire body of an adult, comprising a support; a plurality of first elongated tubular lamps each having a first end and a second end and each arranged to emit ultraviolet radiation primarily or exclusively in the UVA range with no emission in the UVC range, said lamps being mounted in said support in substantial parallelism with one another so that neighboring lamps define gaps of predetermined width; and means for intensifying radiation reaching the head of the person who is exposed to radiation issuing from said lamps including a plurality of second elongated tubular U-shaped lamps mounted on said support in selected ones of said gaps, each of said second lamps being shorter than a first lamp and said second lamps being adjacent the ends of said first lamps and being arranged to emit ultraviolet radiation primarily or exclusively in the UVA range with no emission in the UVC range, each of said second lamps having a diameter less than the width of a gap.

2. The apparatus of claim 1, wherein said first lamps include first and second outer lamps and a plurality of intermediate lamps between said first and second outer lamps, the length of said intermediate lamps matching the length of said outer lamps and said second lamps alternating with and being adjacent the first ends of said intermediate lamps.

3. The apparatus of claim 1, wherein each second lamp has a diameter less than 22 mm.

4. The apparatus of claim 3, wherein the diameters of said second lamps equal or approximate 15 mm.

5. The apparatus of claim 1, wherein the length of each second lamp is between 400 and 500 mm.

6. The apparatus of claim 1, wherein each of said second lamps is has two free ends, said support having sockets for the free ends of said second lamps.

7. The apparatus of claim 6, wherein each of said first lamps has a first end and a second end, said support having sockets for the ends of said first lamps and for the free ends of said second lamps, the sockets for the first ends of said first lamps being disposed at a first distance from the sockets for the second ends of the respective first lamps and the sockets for the free ends of the second lamps being disposed at a greater second distance from the sockets for the second ends of said first lamps.

8. The apparatus of claim 1, wherein the length of each first lamp equals or approximates 176 cm.

9. The apparatus of claim 1, wherein the total number of first lamps is between 9 and 13

10. The apparatus of claim 9, wherein the total number of second lamps is between 3 and 7.

11. The apparatus of claim 1, further comprising reflectors provided on said support intermediate each second lamp and the neighboring first lamps.

12. The apparatus of claim 11, wherein each of said reflectors has a first surface arranged to reflect radiation issuing from the respective second lamp and a second surface arranged to reflect radiation issuing from the respective first lamp.

13. The apparatus of claim 1, further comprising a reflector disposed behind said second lamps and the adjacent portions of those first lamps which alternate with said second lamps, said reflector having a radiation reflecting surface facing said second lamps and said portions of first lamps, said surface having ridges behind said second lamps and behind those portions of first lamps which alternate with said second lamps.

14. The apparatus of claim 1, wherein each of said second lamps emits ultraviolet radiation only in the UVA range.

15. The apparatus of claim 1, wherein said support transmits ultraviolet radiation and is disposed at a level above said lamps.

16. The apparatus of claim 1, wherein said lamps are disposed at a level below said support and are arranged to emit ultraviolet radiation downwardly.

17. The apparatus of claim 1, wherein the total number of first lamps is twelve and the total number of second lamps is five, said first lamps including four first outer lamps, four second outer lamps and four intermediate lamps each of which is flanked by a pair of second lamps.

18. The apparatus of claim 1, wherein each of said second lamps has two free ends disposed at different levels.

* * * * *